United States Patent [19]

Griat et al.

[11] 4,364,930

[45] Dec. 21, 1982

[54] COSMETIC OR PHARMACEUTICAL COMPOSITIONS IN THE FORM OF STABLE OIL-IN-WATER EMULSIONS

[75] Inventors: Jacqueline Griat, Ablon; Arlette Zabotto; Constantin Koulbanis, both of Paris, all of France

[73] Assignee: Societe Anonyme dite: L'OREAL, Paris, France

[21] Appl. No.: 245,207

[22] Filed: Mar. 18, 1981

[30] Foreign Application Priority Data

Mar. 24, 1980 [FR] France ................................. 80 06468

[51] Int. Cl.³ .................... A61K 31/78; A61K 35/12; A61K 7/42; A61K 7/021
[52] U.S. Cl. ......................................... 424/81; 424/63; 424/59; 424/95; 424/359; 252/49.5; 536/18.2
[58] Field of Search ...................... 424/81, 95, 59, 63, 424/359; 252/49.5; 536/4

[56] References Cited

U.S. PATENT DOCUMENTS 2,555,731 6/1951 Cooper .................................. 424/95
3,628,928 12/1971 Goydasch .............................. 536/4

OTHER PUBLICATIONS

Soap/Cosmetics/Chemical Specialties: Nov., 1979, p. 115 and Apr. 1979, p. 128.

Primary Examiner—Donald B. Moyer
Attorney, Agent, or Firm—Cushman, Darby & Cushman

[57] ABSTRACT

A stable oil-in-water emulsion for use in cosmetic or pharmaceutical compositions includes as the emulsifying system therefor a combination of (i) a mixture of (1) mono- or di-alkyl carboxylates of α-methyl glucoside, or a mixture thereof and (2) mono- or di-alkyl carboxylates of α-methyl glucoside polyoxyethylenated with 10–30 moles of ethylene oxide, or a mixture thereof, the said alkyl moiety of each being linear or branched and having from 11–21 carbon atoms, (ii) lecithin, (iii) egg yolk oil, and (iv) a polyacrylic type polymer.

7 Claims, No Drawings

COSMETIC OR PHARMACEUTICAL COMPOSITIONS IN THE FORM OF STABLE OIL-IN-WATER EMULSIONS

The present invention relates to compositions in the form of emulsions and principally to oil-in-water type emulsions for use, generally in cosmetic or pharmaceutical compositions. The oil-in-water emulsions of the present invention exhibit good stability, especially to heat.

The stability of emulsions in cosmetic compositions can be influenced by various factors such as, for example, the presence of electrolytes, the presence of microorganisms, the pH of the substances being dispersed therein, heat and cold, as well as, in certain circumstances, the nature or type of container employed to package the composition.

To a large extent it has been possible to minimize or eliminate any deleterious influence of certain ones of these factors which can cause a rupture or break of the emulsion by judiciously selecting substances or agents for inclusion therein and by employing appropriate packaging means.

However, it has not been possible to reduce in a completely satisfactory manner the incidence of instability of these compositions caused by certain external factors such as cold and, more particularly, heat.

Heat can, in effect, cause a liquefaction of the emulsion and contribute to its rupture or break.

Such disadvantages are encountered principally when there is employed, as emulsifying agents, non-ionic surfactants which are capable of undergoing a hydrolysis reaction. Representative non-ionic surfactants include, for example, esters of fatty acids and polyols such as propylene glycol, glycerine, hexitols and sugars, optionally oxyethylenated or oxypropylated, and, more particularly, when there is employed an emulsifying system constituted by mixtures of a mono- and/or di-alkyl carboxylate of α-methyl glucoside and of a mono- and/or di-alkyl carboxylates of polyoxyethylenated α-methyl glucoside.

While emulsions obtained using these mixtures exhibit excellent properties such as good unctuousness and good spreadability as well as a perceptible jelly texture, they lack storage stability principally when they are stored in a heated atmosphere or enclosure or when, after first use, they are exposed to the sun at elevated temperatures.

In order to remedy this major disadvantage it has been discovered, after numerous tests, that excellent stability can be achieved when this emulsifying system is combined with certain co-emulsifying substances or agents.

Tests carried out over prolonged periods of time have in effect demonstrated that a particular combination of components, on the one hand, preserves the emulsions at relatively high temperatures, in the order of 50° C., without rupturing or breaking the emulsion and, on the other hand, provides emulsions exhibiting, under the microscope, a clearly superior fineness.

The present invention thus relates to a stable composition in the form of an oil-in-water emulsion having an aqueous phase, an oil phase and an emulsifying system, said emulsifying system comprising (i) a mixture of (1) mono- or di-alkyl carboxylates of α-methyl glucoside, or a mixture thereof and (2) mono- or di-alkyl carboxylates of α-methyl glucoside polyoxyethylenated with 10 to 30 moles of ethylene oxide, or a mixture thereof, the said alkyl moiety of each being linear or branched and having from 11 to 21 carbon atoms, (ii) lecithin, (iii) egg yolk oil, and (iv) a polyacrylic type polymer.

Tests carried out over a period of time in the order of two months, at a temperature of about 50° C. have, in effect, shown that this combination of components is necessary to impart good stability to the emulsions.

In effect when one or more of these components of the emulsifying system of the present invention is eliminated or replaced, the emulsions "break" or rupture, that is to say, a separation of the aqueous phase is observed.

The mono- and/or di-alkyl carboxylates of α-methyl glucoside can be represented by the following formulae:

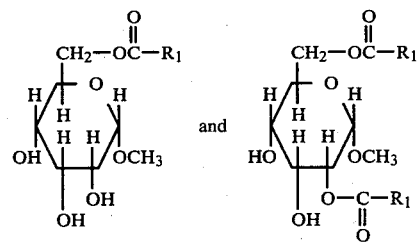

wherein $R_1$ represents a linear or branched alkyl having 11 to 21 carbon atoms.

Representative compounds of this type include, in particular, mono- and/or di-laurate, mono- and/or di-palmitate and mono- and/or di-stearate of α-methyl glucoside and, principally, the sesquistearate of α-methyl glucoside sold by Amerchol under the commercial name of "Glucate SS" ($R_1=C_{17}H_{35}$) which is provided in the form of a mixture of mono- and di-stearates.

The mono- and/or di-alkyl carboxylates of α-methyl glucosides polyoxyethylenated with 10-30 moles of ethylene oxide can be represented by the following formulae:

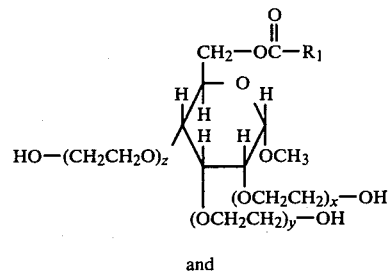

and

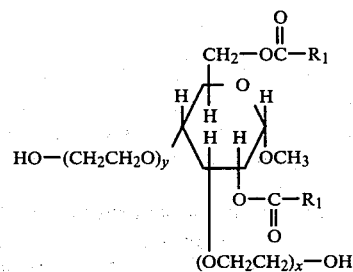

wherein: $R_1$ represents a linear or branched alkyl having from 11 to 21 carbon atoms and $x+y$ $(+z)$ represents 10 to 30 inclusive.

Representative compounds of this type include, in particular, the mono- and/or di-laurate, the mono- and/or di-palmitate and the mono- and/or di-stearate of polyoxyethylenated α-methyl glucoside and, more particularly, the sesquistearate of α-methyl glucoside polyoxyethylenated with 20 moles of ethylene oxide sold by Amerchol under the commercial name of "Glucamate SSE-20" ($R_1=C_{17}H_{35}$ and $x+y$ $(+z)=20$) which is provided in the form of a mixture of mono- and di-stearates.

In the emulsions of the present invention there is employed, preferably a mixture of (1) mono- or di-alkyl carboxylates of α-methyl glucoside, or a mixture thereof, and (2) mono- or dialkyl carboxylates of polyoxyethylenated α-methyl glucoside wherein the weight ratio of (1) to (2) ranges from 40-60:60-40, and, preferably, 50:50.

This mixture of (1) and (2) is employed in the emulsion of the present invention in an amount between about 3 and 15 percent relative to the total weight of the emulsion.

The lecithin can be of vegetable origin, and is, principally, soy lecithin, or egg lecithin.

Lecithins, as is known, are glycerides containing generally two ester groups of different fatty acids (for example, stearic acid and oleic acid) and a phosphocholine group. Such compounds can be represented by the following formula:

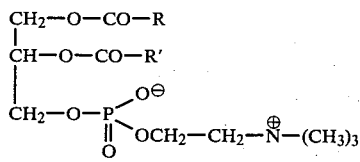

wherein R and R' represent a different fatty acid residue (for example $R=C_{17}H_{35}$ and $R'=C_{17}H_{33}$).

The amount by weight of lecithin relative to the total weight of the emulsion is generally between 0.03 and 1.2 percent.

The egg yolk oil is a fatty body obtained from fresh egg yolks by extraction using ethylene chloride. This oil contains, principally, fatty glycerides, cholesterol and lecithin. It is amber colored, soluble in most organic solvents and miscible with other oils.

The amount of egg yolk oil in the emulsion of the present invention is generally between 0.3 and 4 weight percent based on the total weight of the composition.

The weight ratio of egg yolk oil to lecithin is preferably between 70-95:30-5.

The polyacrylic type polymer used in the emulsifying system according to the present invention can be a cross-linked polyacrylic acid, such as those known under the commercial names of "Carbopol 934" or "Carbopol 940" sold by Goodrich Chemical, which are partially or totally neutralized with an organic base, such as triethanolamine.

In accordance with the present invention, the polyacrylic type polymer is present, preferably, in an amount between 0.1 and 0.5 weight percent based on the total weight of the composition.

The "oil" phase of the emulsion represents about 15 to 60 percent of the total weight thereof and comprises, essentially, one or more fatty bodies such as:
- a mineral oil, for example, petrolatum oil,
- a vegetable or animal oil, modified or not, such as sweet almond oil, avocado oil, calophyllum oil, ricin oil, olive oil, lanolin and its derivatives and perhydrosqualene, and
- a saturated ester or synthetic oil such as ethyl palmitate, isopropyl palmitate, alkyl myristates such as those of isopropyl, butyl and cetyl, hexyl stearate, triglycerides of octanoic and decanoic acids, cetyl ricinoleate, stearyl octanoate (Purcellin oil) and hydrogenated polyisobutene.

The oil phase of the emulsion can also contain certain waxes and principally carnauba wax, beeswax, ozokerite, candelilla wax and micro-crystalline waxes, or even silicone oils, for example, dimethyl polysiloxane.

The aqueous phase of the emulsion represents about 40 to 85 percent by weight based on the total weight of the emulsion.

Cosmetic compositions according to the invention can also contain various components usually present in this type of composition such as, for example, preservative agents, perfumes, dyes, sunscreen agents, pigments, solvents, active agents and the like.

The compositions according to the present invention can be provided in various forms and principally in the form of hydrating creams, for example, sun creams, face creams, body or hand creams, or in the form of a hydrating rouge or even in the form of massage creams, colored creams, body milks, foundation cream or mascaras.

The compositions according to the invention can also be used for the production of pharmaceutical excipients for various active products and can be provided in the form of creams, balms, ointments and the like.

In Table I, below, are listed several stability tests carried out using the oil-in-water emulsions of various compositions. These tests have been conducted by placing the emulsions in an enclosure heated to a temperature of 47° C.±2° C. for a period of 2 months. The control has been carried out every two days.

It can be seen that only emulsion H, made in accordance with the present invention, exhibits a stability greater than 60 days. This shows the importance of the presence of the components in the emulsifying system according to the present invention.

TABLE I

| Example | A | B | C | D | E | F | G | H |
|---|---|---|---|---|---|---|---|---|
| Glucate SS | 4g | 4g | 4g | 4g | 4g | 4g | 4g | 4g |
| Glucate SSE 20 | 4g | 4g | 4g | 4g | 4g | 4g | 4g | 4g |
| Lecithin | | 0.45g | | | 0.45g | | 0.45g | 0.45g |
| Egg Yolk Oil | | | 2.25g | | | 2.25g | 2.25g | 2.25g |
| Carbopol 934 | | | | 0.3g | 0.3g | 0.3g | | 0.3g |
| Triethanolamine | | | | 0.3g | 0.3g | 0.3g | | 0.3g |
| Oil Phase: | | | | | | | | |
| Petrolatum Oil | 40g | 40g | 40g | 40g | 40g | 40g | 40g | 40g |
| Isopropyl palmitate | 5g | 5g | 5g | 5g | 5g | 5g | 5g | 5g |
| Preservative | 0.3g | 0.3g | 0.3g | 0.3g | 0.3g | 0.3g | 0.3g | 0.3g |
| Perfume | 0.3g | 0.3g | 0.3g | 0.3g | 0.3g | 0.3g | 0.3g | 0.3g |
| Water phase, sufficient for | 100g | 100g | 100g | 100g | 100g | 100g | 100g | 100g |
| Time of rupture in days at 47° C. | | | | | | | | |

TABLE I-continued

| Example | A | B | C | D | E | F | G | H |
|---|---|---|---|---|---|---|---|---|
| ± 2° C. | <30 | <30 | <30 | <40 | <40 | <30 | <30 | >60 |

To better understand the present invention the following non-limiting examples of the compositions of the present invention, in the form of oil-in-water emulsions, are given.

EXAMPLE 1

In accordance with the present invention a day cream in the form of an oil-in-water emulsion is prepared by admixing the following components:

"Glucate SS", sold by Amerchol: 4.8 g
"Glucamate SSE 20", sold by Amerchol: 3.2 g
Soy lecithin: 0.2 g
Egg Yolk Oil: 0.5 g
Sweet almond oil: 10 g
Perhydrosqualene: 10 g
"Carbopol 934", sold by Goodrich: 0.3 g
Triethanolamine: 0.3 g
Perfume: 0.3 g
Methyl parahydroxybenzoate: 0.3 g
Sterile, demineralized water, sufficient for: 100 g

EXAMPLE 2

A body milk in the form of an oil-in-water emulsion is prepared by admixing the following components:

"Glucate SS": 3 g
"Glucamate SSE 20": 3 g
Egg lecithin: 0.4 g
Egg Yolk Oil: 1.6 g
Petrolatum Oil: 10 g
Lanolin alcohol: 2 g
Isopropyl palmitate: 5 g
"Carbopol 934": 0.3 g
Triethanolamine: 0.3 g
Propylene glycol: 2 g
Perfume: 1 g
Methyl parahydroxybenzoate: 0.3 g
Sterile, demineralized water, sufficient for: 100 g

EXAMPLE 3

A colored day cream in the form of an oil-in-water emulsion is prepared by admixing the following components:

"Glucate SS": 4 g
"Glucamate SSE20": 4 g
Soy lecithin: 0.3 g
Egg Yolk Oil: 2.7 g
Volatile silicone oil (polymethyl siloxane): 15 g
Perhydrosqualene: 15 g
"Carbopol 934": 0.3 g
Triethanolamine: 0.3 g
Yellow iron oxide: 0.4 g
Red iron oxide: 0.5 g
Titanium oxide: 1 g
Methyl parahydroxybenzoate: 0.3 g
Perfume: 0.3 g
Sterile, demineralized water, sufficient for: 100 g

EXAMPLE 4

A cream for the care of the face in the form of an oil-in-water emulsion is prepared by admixing the following components:

"Glucate SS": 4 g
"Glucamate SSE 20": 6 g
Soy lecithin: 1 g
Egg Yolk Oil: 2.5 g
Petrolatum oil: 30 g
Perhydrosqualene: 10 g
"Carbopol 934": 0.3 g
Triethanolamine: 0.3 g
Placental extract: 5 g
Methyl parahydroxybenzoate: 0.3 g
Perfume: 0.3 g
Sterile, demineralized water, sufficient for: 100 g

What is claimed is:

1. An oil-in-water emulsion comprising 15 to 60 percent by weight of an oil phase, 40 to 85 percent by weight of an aqueous phase and an effective amount of an emulsifying agent, said emulsifying agent comprising
   (i) a mixture of (1) an alkyl carboxylate of α-methyl glucoside, wherein the alkyl carboxylate moiety is selected from the group consisting of mono-laurate, di-laurate, mono-palmitate, di-palmitate, mono-stearate and di-stearate, or a mixture of said alkyl carboxylates of α-methyl glucoside and (2) an alkyl carboxylate of α-methyl glucoside polyoxyethylenated with 10–30 moles of ethylene oxide wherein the alkyl carboxylate moiety is selected from the group consisting of mono-laurate, di-laurate, mono-palmitate, di-palmitate, mono-stearate and di-stearate, or a mixture of said polyoxyethylenated alkyl carboxylates of α-methyl glucoside, the weight ratio of (1) to (2) ranging from 40-60:60-40, said mixture of (1) and (2) being present in an amount of about 3 to 15 percent by weight based on the total weight of said emulsion,
   (ii) vegetable lecithin or egg lecithin, present in an amount of about 0.03 to 1.2 percent by weight based on the total weight of said emulsion,
   (iii) egg yolk oil present in an amount of about 0.3 to 4 percent by weight based on the total weight of said emulsion, and
   (iv) a water soluble acrylic acid polymer present in an amount of about 0.1 to 0.5 percent by weight based on the total weight of said emulsion.

2. The oil-in-water emulsion of claim 1 wherein said water soluble acrylic acid polymer is neutralized with triethanolamine.

3. The oil-in-water emulsion of claim 1 wherein the ratio of (1) to (2) is 50:50.

4. The oil-in-water emulsion of claim 1 wherein the vegetable lecithin is soy lecithin.

5. The oil-in-water emulsion of claim 1 wherein the weight ratio of egg yolk oil to the said vegetable lecithin or egg lecithin is 70-95:30-5.

6. The oil-in-water emulsion of claim 1 wherein (1) is mono-sesquistearate or di-sesquistearate of α-methyl glucoside.

7. The oil-in-water emulsion of claim 1 wherein (2) is mono-sesquistearate or di-sesquistearate of α-methyl glucoside polyoxyethylenated with 20 moles of ethylene oxide.

* * * * *